(12) United States Patent
Pinto

(10) Patent No.: US 11,705,232 B2
(45) Date of Patent: Jul. 18, 2023

(54) COMMUNICATION SYSTEM AND METHOD

(71) Applicant: Nuance Communications, Inc., Burlington, MA (US)

(72) Inventor: Joel Praveen Pinto, Aachen (DE)

(73) Assignee: Nuance Communications, Inc., Burlington, MA (US)

( * ) Notice: Subject to any disclaimer, the term of this patent is extended or adjusted under 35 U.S.C. 154(b) by 0 days.

(21) Appl. No.: 17/669,099

(22) Filed: Feb. 10, 2022

(65) Prior Publication Data

US 2022/0254464 A1    Aug. 11, 2022

Related U.S. Application Data

(60) Provisional application No. 63/148,438, filed on Feb. 11, 2021.

(51) Int. Cl.
| | |
|---|---|
| *G06F 17/00* | (2019.01) |
| *G16H 15/00* | (2018.01) |
| *G06F 40/40* | (2020.01) |
| *G06F 3/01* | (2006.01) |
| *G10L 15/26* | (2006.01) |
| *G06F 40/186* | (2020.01) |

(52) U.S. Cl.
CPC .............. *G16H 15/00* (2018.01); *G06F 3/013* (2013.01); *G06F 40/186* (2020.01); *G06F 40/40* (2020.01); *G10L 15/26* (2013.01)

(58) Field of Classification Search
CPC ......... G16H 15/00; G10L 15/26; G06F 3/013; G06F 40/186; G06F 40/40; G06F 40/56
See application file for complete search history.

(56) References Cited

U.S. PATENT DOCUMENTS

| | | | | |
|---|---|---|---|---|
| 10,564,714 | B2 * | 2/2020 | Marggraff | G06F 3/04886 |
| 11,217,033 | B1 * | 1/2022 | Morgan | G16H 20/60 |
| 11,515,020 | B2 * | 11/2022 | Vozila | G16H 15/00 |
| 2008/0062382 | A1 * | 3/2008 | Endrikhovski | G06F 3/013 351/209 |
| 2008/0103828 | A1 * | 5/2008 | Squilla | G16H 15/00 715/201 |
| 2008/0255949 | A1 * | 10/2008 | Genco | A61B 5/165 705/14.4 |
| 2011/0111384 | A1 * | 5/2011 | Dietrich | A61B 5/18 434/350 |
| 2012/0179670 | A1 * | 7/2012 | Burke | G06F 16/583 707/E17.014 |

(Continued)

FOREIGN PATENT DOCUMENTS

| | | | | |
|---|---|---|---|---|
| WO | WO-2017189758 | A1 * | 11/2017 | G06F 3/013 |
| WO | 2020121382 | A1 | 6/2020 | |

OTHER PUBLICATIONS

International Search Report and Written Opinion issued in International Application No. PCT/US2022/015995 dated May 24, 2022.

*Primary Examiner* — Laurie A Ries
(74) *Attorney, Agent, or Firm* — Brian J. Colandreo; Heath M. Sargeant; Holland & Knight LLP

(57) ABSTRACT

A method, computer program product, and computing system for receiving audio-based content from a user who is reviewing an image on a display screen; receiving gaze information that defines a gaze location of the user; and temporally aligning the audio-based content and the gaze information to form location-based content.

27 Claims, 9 Drawing Sheets

(56) References Cited

U.S. PATENT DOCUMENTS

| | | | | |
|---|---|---|---|---|
| 2013/0024208 | A1* | 1/2013 | Vining | A61B 6/5217 |
| | | | | 705/3 |
| 2013/0187835 | A1* | 7/2013 | Vaught | G06F 3/011 |
| | | | | 345/7 |
| 2013/0262113 | A1* | 10/2013 | Oz | G06F 40/174 |
| | | | | 704/235 |
| 2014/0375558 | A1* | 12/2014 | Conness | H04N 21/4223 |
| | | | | 345/156 |
| 2016/0171299 | A1* | 6/2016 | Lee | G06F 3/04842 |
| | | | | 382/128 |
| 2017/0193182 | A1* | 7/2017 | Mihai | G16H 80/00 |
| 2017/0337329 | A1* | 11/2017 | Liu | A61B 6/463 |
| 2018/0177973 | A1* | 6/2018 | Keene | A61B 5/486 |
| 2018/0350459 | A1* | 12/2018 | Yang | G06F 18/217 |
| 2019/0139642 | A1* | 5/2019 | Roberge | G06F 3/013 |
| 2019/0304582 | A1* | 10/2019 | Blumenthal | G16H 40/67 |
| 2019/0324533 | A1* | 10/2019 | Itkowitz | G06F 3/013 |
| 2020/0234809 | A1* | 7/2020 | Huynh | G16H 15/00 |
| 2020/0337627 | A1* | 10/2020 | Penney | G09B 19/00 |
| 2021/0076002 | A1* | 3/2021 | Peters | G06V 40/20 |
| 2021/0216822 | A1* | 7/2021 | Paik | G06F 3/013 |
| 2021/0303107 | A1* | 9/2021 | Pla I Conesa | G06F 3/017 |
| 2022/0044772 | A1* | 2/2022 | Moghadam | A61B 5/7455 |
| 2022/0054006 | A1* | 2/2022 | Clarida | G16H 30/40 |
| 2022/0093094 | A1* | 3/2022 | Krishnan | G06V 10/40 |
| 2022/0115022 | A1* | 4/2022 | Sharifi | G10L 15/22 |
| 2023/0019463 | A1* | 1/2023 | Duke | G10L 21/055 |

* cited by examiner

COMMUNICATION SYSTEM AND METHOD

RELATED APPLICATION(S)

This application claims the benefit of U.S. Provisional Application No. 63/148,438, filed on 11 Feb. 2021; the entire contents of which is herein incorporated by reference.

TECHNICAL FIELD

This disclosure relates to communication systems and methods and, more particularly, to communication systems and methods for use by medical professional.

BACKGROUND

As is known in the art, medical processionals may use various computer systems to perform their job. For example, various processionals may use computer systems to review pieces of medical information, train AI models, interact with patients, etc.

During such use, these professionals may utter various commands and provide verbal information to such computing systems Often times, such verbal information may be associated with/related to a specific portion of an image being viewed by the medical professional. But unfortunately, such verbal information may not identify what the medical professional is actually referring to/looking at.

SUMMARY OF DISCLOSURE

In one implementation, a computer-implemented method is executed on a computing device and includes: receiving audio-based content from a user who is reviewing an image on a display screen; receiving gaze information that defines a gaze location of the user; and temporally aligning the audio-based content and the gaze information to form location-based content.

One or more of the following features may be included. The image may be rendered on the display screen. The audio-based content and the gaze information may be generated during a telehealth session. The audio-based content and the gaze information may be generated during a diagnostic session. The audio-based content and the gaze information may be generated during AI model training session. The location-based content may be utilized to populate a medical report. The location-based content may be utilized to train an AI model. The location-based content may be utilized to enrich a medical image. The audio-based content may be descriptive content that describes a portion of the medical image. The gaze information may define a gaze location of the user with respect to a portion of the image on a display screen.

In another implementation, a computer program product resides on a computer readable medium and has a plurality of instructions stored on it. When executed by a processor, the instructions cause the processor to perform operations including: receiving audio-based content from a user who is reviewing an image on a display screen; receiving gaze information that defines a gaze location of the user; and temporally aligning the audio-based content and the gaze information to form location-based content.

One or more of the following features may be included. The image may be rendered on the display screen. The audio-based content and the gaze information may be generated during a telehealth session. The audio-based content and the gaze information may be generated during a diagnostic session. The audio-based content and the gaze information may be generated during AI model training session. The location-based content may be utilized to populate a medical report. The location-based content may be utilized to train an AI model. The location-based content may be utilized to enrich a medical image. The audio-based content may be descriptive content that describes a portion of the medical image. The gaze information may define a gaze location of the user with respect to a portion of the image on a display screen.

In another implementation, a computing system includes a processor and memory is configured to perform operations including: receiving audio-based content from a user who is reviewing an image on a display screen; receiving gaze information that defines a gaze location of the user; and temporally aligning the audio-based content and the gaze information to form location-based content.

One or more of the following features may be included. The image may be rendered on the display screen. The audio-based content and the gaze information may be generated during a telehealth session. The audio-based content and the gaze information may be generated during a diagnostic session. The audio-based content and the gaze information may be generated during AI model training session. The location-based content may be utilized to populate a medical report. The location-based content may be utilized to train an AI model. The location-based content may be utilized to enrich a medical image. The audio-based content may be descriptive content that describes a portion of the medical image. The gaze information may define a gaze location of the user with respect to a portion of the image on a display screen.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
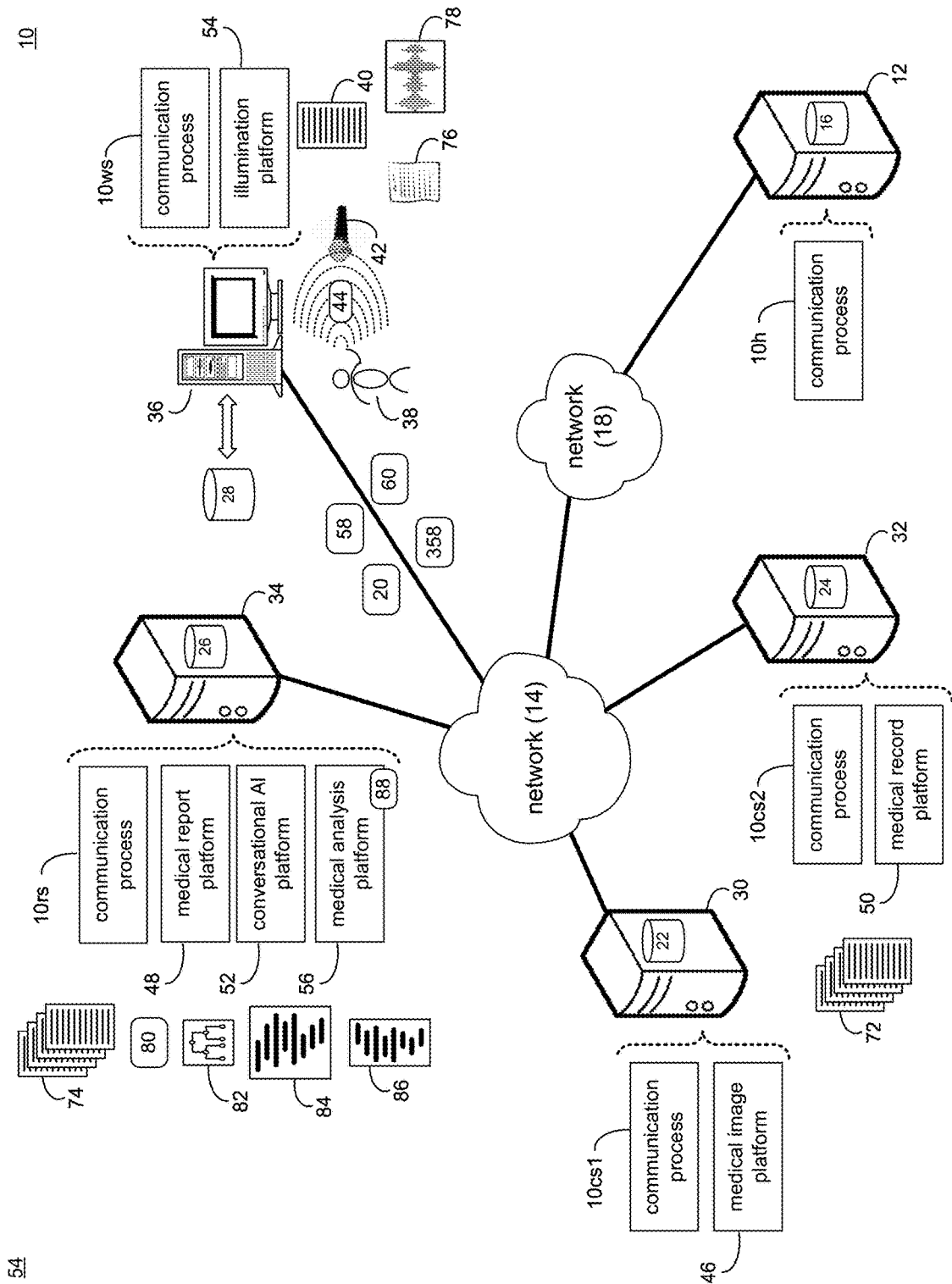
FIG. 1 is a diagrammatic view of a plurality of disparate systems that communicate via a communication process coupled to a distributed computing network.

Referring to FIG. 1, there is shown communication process 10. As will be discussed below in greater detail, communication process 10 may be configured to allow for the communication and transfer of data between various disparate systems.

Communication process 10 may be implemented as a server-side process, a client-side process, or a hybrid server-side/client-side process. For example, communication process 10 may be implemented as a purely server-side process via communication process 10$h$. Alternatively, communication process 10 may be implemented as a purely client-side process via one or more of communication process 10$cs$1, communication process 10$cs$2, communication process 10$rs$, and communication process 10$ws$. Alternatively still, communication process 10 may be implemented as a hybrid server-side/client-side process via communication process 10$h$ in combination with one or more of communication process 10$cs$1, communication process 10$cs$2, communication process 10$rs$, and communication process 10$ws$.

Accordingly, communication process 10 as used in this disclosure may include any combination of communication process 10$h$, communication process 10$cs$1, communication process 10$cs$2, communication process 10$rs$, and communication process 10$ws$.

Communication process 10$h$ may be a server application and may reside on and may be executed by communication computing system 12, which may be connected to network 14 (e.g., the Internet or a local area network). Communication computing system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of communication computing system 12 may execute one or more operating systems, examples of which may include but are not limited to: Microsoft Windows Server™; Redhat Linux™, Unix, or a custom operating system, for example.

The instruction sets and subroutines of communication process 10$h$, which may be stored on storage device 16 coupled to communication computing system 12, may be executed by one or more processors (not shown) and one or more memory architectures (not shown) included within communication computing system 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; an intranet; or the internet. Accordingly, network 14 may be a local area network and network 18 may be the internet, thus allowing communication process 10$h$ to be a cloud-based resource.

Various pieces of data (e.g., data 20) may be transferred between communication process 10$h$, communication process 10$cs$1, communication process 10$cs$2, communication process 10$rs$, and communication process 10$ws$. Examples of data 20 may include but are not limited to data requests (e.g., data read requests and data write requests) and the related data itself.

The instruction sets and subroutines of communication process 10$cs$1, communication process 10$cs$2, communication process 10$rs$, and communication process 10$ws$, which may be stored on storage devices 22, 24, 26, 28 (respectively) coupled to computing systems 30, 32, 34, 36 (respectively), may be executed by one or more processors (not shown) and one or more memory architectures (not shown) incorporated into computing systems 30, 32, 34, 36 (respectively). Examples of storage devices 22, 24, 26, 28 may include but are not limited to: hard disk drives; optical drives; RAID devices; random access memories (RAM); read-only memories (ROM), and all forms of flash memory storage devices. Examples of computing systems 30, 32, 34, 36 may include, but are not limited to, collaborating computing system 30 (e.g., a personal computer, a workstation computer, a server computer, and a cloud-based resource), collaborating computing system 32 (e.g., a personal computer, a workstation computer, a server computer, and a cloud-based resource), report computing system 34 (e.g., a personal computer, a workstation computer, a server computer, and a cloud-based resource), and workstation computing system 36 (e.g., a smart telephone, a tablet computer, a notebook computer, a laptop computer, a personal computer, a workstation computer, a server computer, and a cloud-based resource).

As will be discussed below in greater detail, the above-described platform (e.g., communication process 10 in combination with computing systems 12, 30, 32, 34, 36) may be configured to allow clinician 38 (e.g., a radiologist, a cardiologist or a pathologist) to review medical information (e.g., data 20) and populate medical report 40. The medical information (e.g., data 20) may be provided by one or more of the collaborating systems (e.g., collaborating computing systems 30, 32), examples of which may include but are not limited to a collaborating system executing a PACS system and a collaborating system executing an EHR system.

As is known in the art, a PACS (Picture Archiving and Communication System) system is a medical imaging technology that provides economical storage and convenient access to images from multiple modalities (source machine types). Electronic images and reports may be transmitted digitally via PACS; thus eliminating the need to manually file, retrieve and/or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM. Examples of such medical imagery stored and served by such a PACS system may include but are not limited to X-ray imagery, CT imagery, MRI imagery, and ultrasound imagery.

As is known in the art, an EHR (Electronic Health Record) system is a systematized collection of patient and population electronically stored health information in a digital format. These records may be shared across different health care settings, wherein records may be shared through network-connected, enterprise-wide information systems or other information networks and exchanges. An EHR system may define a range of data, including demographics, medical histories, medications and allergies, immunization status, laboratory test results, radiology images, vital signs, personal statistics, and billing information.

Accordingly and as will be discussed below in greater detail, clinician 38 may utilize workstation computing system 36 to review medical information (e.g., data 20) provided by the collaborating systems (e.g., collaborating computing systems 30, 32). Report computing system 34 may be configured to allow clinician 38 to populate medical report (e.g., medical report 40). Communication process 10 may be configured to allow clinician 38 to utilize audio input device 42 to provide verbal information/command 44 based upon information ascertained from the medical information (e.g., data 20).

Examples of audio input device 42 may include but are not limited to a lapel microphone, a desktop microphone, a wall-mounted microphone, or a device-embedded microphone (e.g., a microphone embedded into a laptop computer). As will be discussed below in greater detail, communication computing system 12 may be configured to allow all of the computing systems (e.g., computing systems 12, 30, 32, 34, 36) within the above-described platform to communicate with each other and exchange information (e.g., data 20).

General Intersystem Communication

Figure 2:
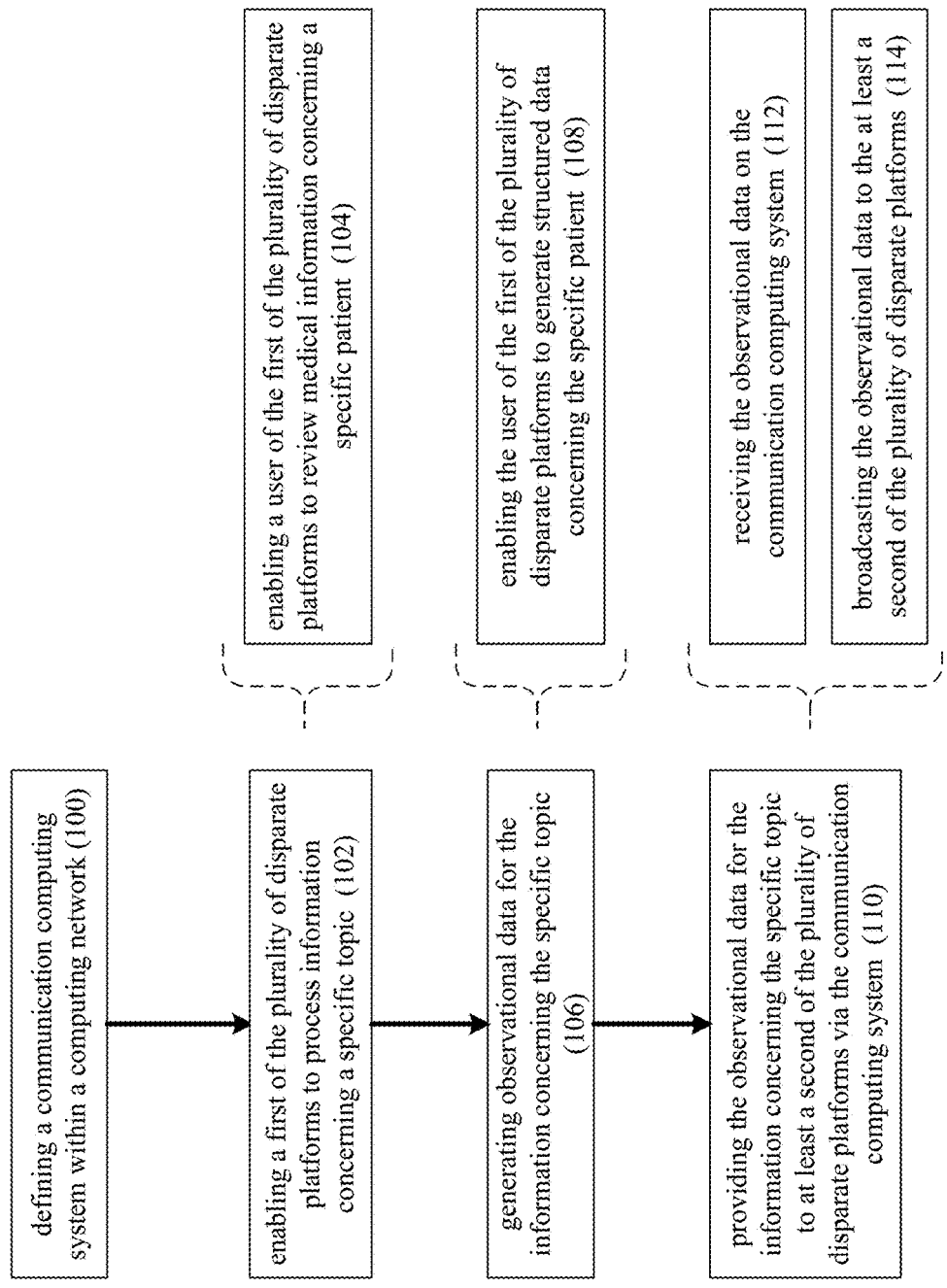
FIG. 2 is a flow chart of one implementation of the communication process of FIG. 1 according to an implementation of this disclosure.

Referring also to FIG. 2, communication process 10 may define 100 a communication computing system (e.g., communication computing system 12) within a computing network (e.g., network 14 and/or network 18). The communication computing system (e.g., communication computing system 12) may be configured as a local system or as a remote system. For example, communication computing system 12 may be a local computing system directly coupled to e.g., computing systems 30, 32, 34, 36 via a local area network (e.g., network 14). Additionally/alternatively, communication computing system 12 may be a cloud-based computing system (e.g., a cloud-based resource) indirectly coupled to e.g., computing systems 30, 32, 34, 36 via network 18 (e.g., the internet). As will be discussed below in greater detail, communication computing system 12 (in combination with communication process 10) may be configured to effectuate communication between computing systems 30, 32, 34, 36.

As discussed above, this computing network (e.g., network 14 and/or network 18) may couple various computing systems (e.g., computing systems 12, 30, 32, 34, 36) configured to provide information (e.g., data 20) concerning various topics. Disparate platforms executed on these computing systems (e.g., computing systems 12, 30, 32, 34, 36) may generate and/or modify information (e.g., data 20), which may be provided to other computing systems within the computing network (e.g., network 14 and/or network 18). For example, a disparate platform executed on collaborating computing system 30 may generate information (e.g., data 20) that may be provided to workstation computing system 36 via the computing network (e.g., network 14 and/or network 18).

As discussed above, communication process 10 may be configured to allow clinician 38 (e.g., a radiologist, a cardiologist or a pathologist) to utilize workstation computing system 36 to review medical information (e.g., data 20) concerning various patients and populate various medical reports (e.g., medical report 40). Accordingly, the plurality of disparate platforms executed on these computing systems (e.g., computing systems 12, 30, 32, 34, 36) may include a plurality of disparate medical platforms (e.g., medical imaging platform 46; medical report platform 48; medical record platform 50; conversational AI platform 52; illumination platform 54 and/or medical analysis platform 56.

Figure 3:
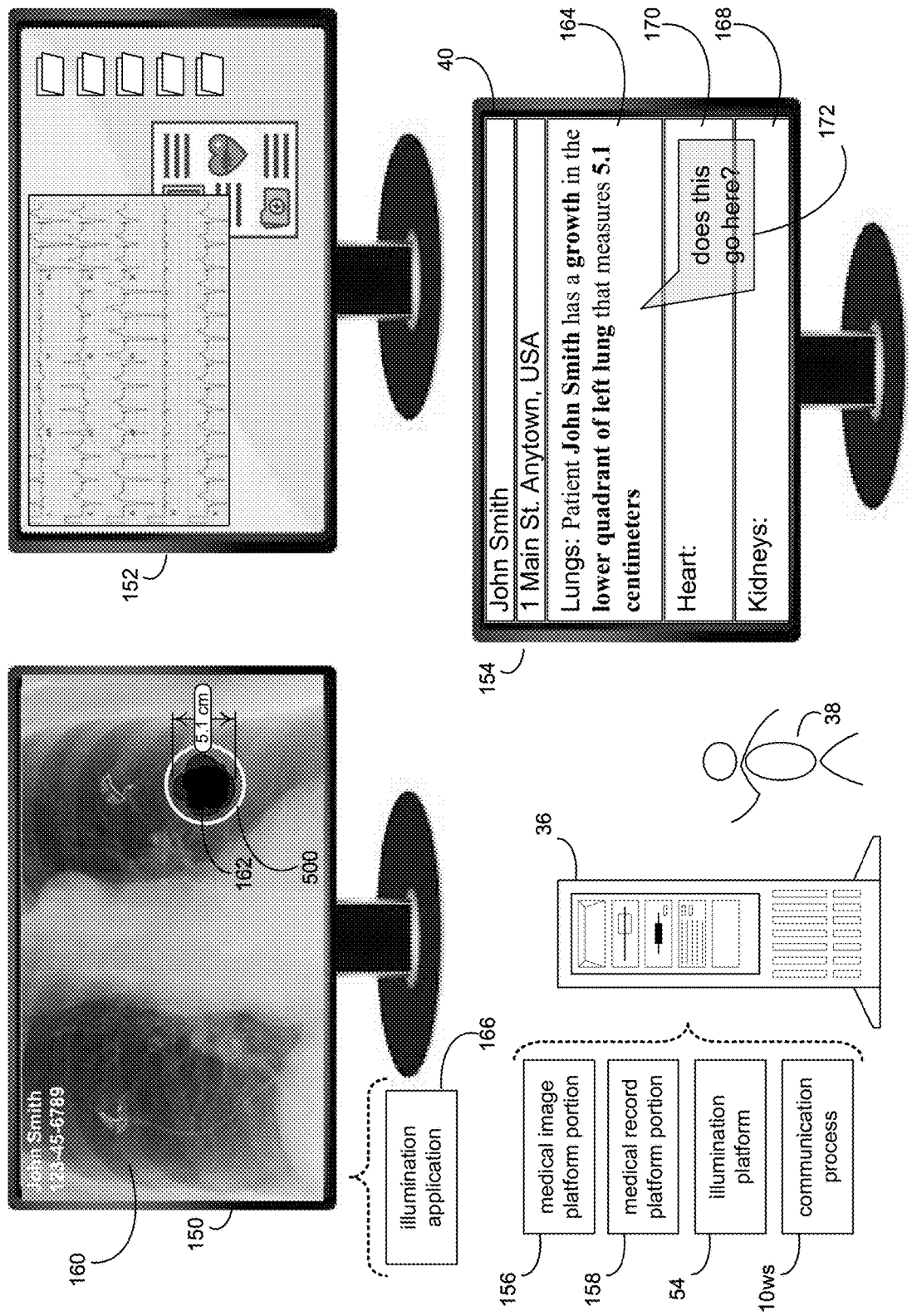
FIG. 3 is a diagrammatic view of a workstation computing system executing the communication process of FIG. 1.

At least a portion of the plurality of disparate platforms (e.g., disparate platforms 46, 48, 50, 52, 54, 56) may be executed on a single computing system. For example and referring also to FIG. 3, workstation computing system 36 may be configured to support multiple monitors (e.g., monitors 150, 152, 154), which may be simultaneously used by clinician 38 to access and utilize the various disparate platforms (e.g., disparate platforms 46, 48, 50, 52, 54, 56).

In this example, monitor 150 is shown to allow clinician 38 to access medical imaging platform 46, wherein monitor 152 is shown to allow clinician 38 to access medical record platform 50. Assume for this example that medical imaging platform 46 is being executed on collaborating system 30, while medical record platform 50 is being executed on collaborating system 32. Accordingly, at least a portion of medical imaging platform 46 and at least a portion of medical record platform 50 may be executed on a single computing system (e.g., workstation computing system 36), wherein:

medical image platform portion 156 may interact with medical image platform 46 being executed on collaborating system 30 and may enable clinician 38 to review the medical images provided by medical image platform 46 on workstation computing system 36; and medical record platform portion 158 may interact with medical record platform 50 being executed on collaborating system 32 and may enable clinician 38 to review the medical records provided by medical record platform 50 on workstation computing system 36.

Communication process 10 may enable 102 a first of the plurality of disparate platforms (e.g., medical image platform 46) to process information (e.g., data 20) concerning a specific topic.

As discussed above, communication process 10 may be configured to allow clinician 38 (e.g., a radiologist, a cardiologist or a pathologist) to utilize workstation computing system 36 to review medical information (e.g., data 20) concerning various patients and populate various medical reports (e.g., medical report 40). Accordingly and when enabling 102 a first of the plurality of disparate platforms (e.g., medical image platform 46) to process information (e.g., data 20) concerning a specific topic (e.g., a specific patient), communication process 10 may enable 104 a user (e.g., clinician 38) of the first of the plurality of disparate platforms (e.g., medical image platform 46) to review medical information (e.g., data 20) concerning a specific patient.

For this example, assume that collaborating system 30 is executing medical image platform 46 (e.g., PACS), wherein medical image platform portion 156 is executed on workstation computing system 36. Accordingly, medical image platform 46 (e.g., PACS) being executed on collaborating system 30 may provide chest x-ray image 160 (e.g., data 20) of a patient (e.g., patient John Smith), wherein clinician 38 may review chest x-ray image 160 using medical image platform portion 156 being executed on workstation computing system 36.

Communication process 10 may generate 106 observational data (e.g., data 58) for the information (e.g., data 20) concerning the specific topic (e.g., a specific patient). For example and when generating 106 observational data (e.g., data 58) for the information (e.g., data 20) concerning the specific topic (e.g., a specific patient), communication process 10 may enable 108 the user (e.g., clinician 38) of the first of the plurality of disparate platforms (e.g., medical image platform 46) to generate structured data concerning the specific patient.

Specifically and with respect to structured data, structured data may relate to a structured observation that is made by (in this example) clinician 38, wherein a structured observation may be codified (have one or more medical codes assigned). For example, a lung may have an assigned medical code . . . and a growth may have an assigned medical code . . . and over 5.0 centimeters may have an assigned medical code.

Accordingly, communication process 10 may enable 104 clinician 38 to review chest x-ray image 160 (via medical image platform portion 156 executed on workstation computing system 36) to generate 106 observational data (e.g., data 58) for chest x-ray image 160 of patient John Smith. Examples of such observational data (e.g., data 58) may include but are not limited to structured data that concerns e.g., measurements of objects within an image (e.g., x-ray image 160), the location of objects within an image (e.g., x-ray image 160), and the type of image (e.g., x-ray image 160).

Accordingly and via medical image platform portion 156 executed on workstation computing system 36, clinician 38 may review chest x-ray image 160. Upon reviewing chest x-ray image 160, clinician 38 may notice a growth (e.g., growth 162) within x-ray image 160. Accordingly and through medical image platform portion 156 executed on workstation computing system 36, communication process 10 may enable 108 clinician 38 to measure growth 162 (measured to be 5.1 centimeters), thus generating 106 observational data (e.g., data 58).

Communication process 10 may provide 110 the observational data (e.g., data 58) for the information (e.g., data 20) concerning the specific topic (e.g., a specific patient) to at least a second of the plurality of disparate platforms (e.g., medical report platform 48) via the communication computing system (e.g., communication computing system 12). For this example, assume that the observational data (e.g., data 58) identifies the location of growth 162 (e.g., lower quadrant of left lung) and the size of growth 162 (e.g., 5.1 centimeters).

When providing 110 the observational data (e.g., data 58) for the information (e.g., data 20) concerning the specific topic (e.g., a specific patient) to at least a second of the plurality of disparate platforms (e.g., medical report platform 48) via the communication computing system (e.g., communication computing system 12), communication process 10 may:
  receive 112 the observational data (e.g., data 58) on the communication computing system (e.g., communication computing system 12); and
  broadcast 114 the observational data (e.g., data 58) to the at least a second of the plurality of disparate platforms (e.g., medical report platform 48).

For example and as discussed above, through medical image platform portion 156 executed on workstation computing system 36, communication process 10 may enable 108 clinician 38 to measure growth 162 (measured to be 5.1 centimeters), thus generating 106 observational data (e.g., data 58). This observational data (e.g., data 58) may then be provided to communication computing system 12. For example, medical image platform portion 156 that is executed on workstation computing system 36 may provide observational data (e.g., data 58) to communication computing system 12. Additionally/alternatively, medical image platform 46 (e.g., PACS) that is executed on collaborating system 30 may provide observational data (e.g., data 58) to communication computing system 12.

Once the observational data (e.g., data 58) is received 112 on the communication computing system (e.g., communication computing system 12), the communication computing system (e.g., communication computing system 12) may broadcast 114 the observational data (e.g., data 58) to the at least a second of the plurality of disparate platforms (e.g., medical report platform 48).

As discussed above, medical report platform 48 may be configured to allow clinician 38 to populate a medical report (e.g., medical report 40) concerning (in this example) patient John Smith. Accordingly and as will be discussed below in greater detail, once the observational data (e.g., data 58) is received 112, the communication computing system (e.g., communication computing system 12) may broadcast 114 the observational data (e.g., data 58) to medical report platform 48 so that the observational data (e.g., data 58) may be utilized to populate a medical report (e.g., medical report 40) for the patient (e.g., patient John Smith). Accordingly, the appropriate field (e.g., field 164) within medical report 40 of patient John Smith may be populated by medical report platform 48 to state that chest x-ray image 160 of patient John Smith shows a 5.1 centimeter growth (e.g., growth 162) in the lower quadrant of the left lung.

Figure 4:
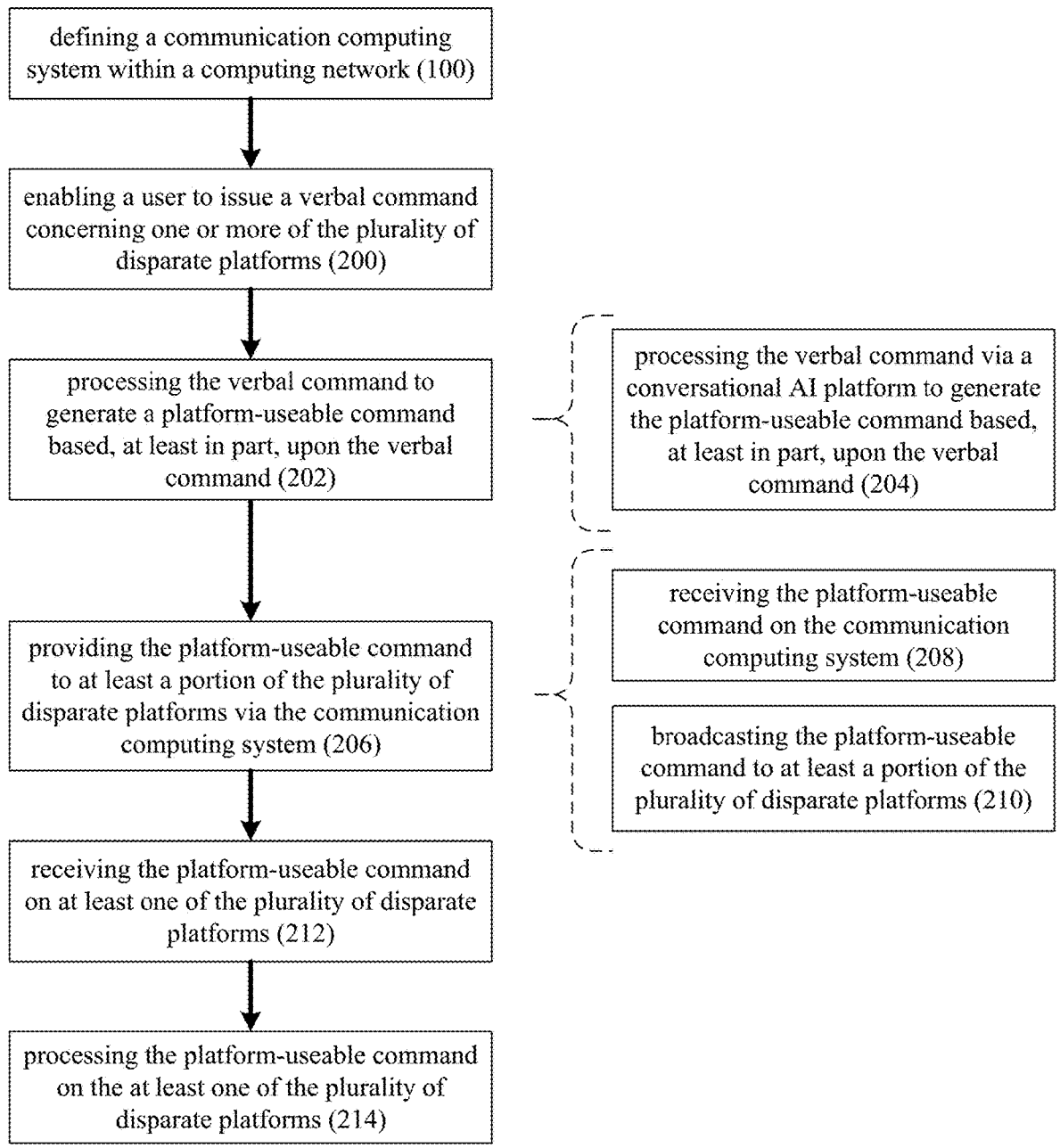
FIG. 4 is a flow chart of another implementation of the communication process of FIG. 1 according to an implementation of this disclosure.

Referring also to FIG. 4 and as discussed above, communication process 10 may define 100 a communication computing system (e.g., communication computing system 12) within a computing network (e.g., network 14 and/or network 18). This computing network (e.g., network 14 and/or network 18) may couple various computing systems (e.g., computing systems 12, 30, 32, 34, 36) configured to provide information (e.g., data 20) concerning various topics. Disparate platforms (e.g., disparate platforms 46, 48, 50, 52, 54, 56) executed on these computing systems (e.g., computing systems 12, 30, 32, 34, 36) may generate and/or modify information (e.g., data 20), which may be provided to other computing systems within the computing network (e.g., network 14 and/or network 18).

Communication process 10 may enable 200 a user (e.g., clinician 38) to issue a verbal command (e.g., verbal information/command 44) concerning one or more of the plurality of disparate platforms (e.g., disparate platforms 46, 48, 50, 52, 54, 56).

As discussed above, communication process 10 may be configured to allow clinician 38 to utilize audio input device 42 to provide verbal information/command 44 based upon information ascertained from the medical information (e.g., data 20). Examples of audio input device 42 may include but are not limited to a lapel microphone, a desktop microphone, a wall-mounted microphone, or a device-embedded microphone (e.g., a microphone embedded into a laptop computer). Accordingly, since communication process 10 enables 200 clinician 38 to issue verbal commands (e.g., verbal information/command 44) concerning the disparate platforms (e.g., disparate platforms 46, 48, 50, 52, 54, 56), communication process 10 may provide clinician 38 with virtual assistant functionality.

Communication process 10 may process 202 the verbal command (e.g., verbal information/command 44) to generate a platform-useable command (e.g., platform-useable command 60) based, at least in part, upon the verbal command (e.g., verbal information/command 44). As discussed above, the plurality of disparate platforms (e.g., disparate platforms 46, 48, 50, 52, 54, 56) may include medical imaging platform 46; medical report platform 48; medical record platform 50; conversational AI platform 52; illumination platform 54 and/or medical analysis platform 56.

When processing 202 the verbal command (e.g., verbal information/command 44) to generate a platform-useable command (e.g., platform-useable command 60) based, at least in part, upon the verbal command (e.g., verbal information/command 44), communication process 10 may process 204 the verbal command (e.g., verbal information/command 44) via a conversational AI platform (e.g., conversational AI platform 52) to generate the platform-useable command (e.g., platform-useable command 60) based, at least in part, upon the verbal command (e.g., verbal information/command 44).

While conversational AI platform 52 is shown to be executed on report computing system 34, this is for illustrative purposes only and is not intended to be a limitation of this disclosure, as other configurations are possible and are considered to be within the scope of this disclosure. For example, conversational AI platform 52 may be executed on any other computing system (e.g., computing systems 12, 30, 32, 36), As is known in the art, conversational AI is a technology that enables speech-based interaction between humans and computing systems. Accordingly, conversational AI platform 52 may process human speech (e.g., verbal information/command 44) to decipher the same so that e.g., a computing system may effectuate a computer-based response and/or render a speech-based response.

Conversational AI platform 52 may utilize Natural Language Understanding (NLU) and Natural Language Processing (NLP). As is known in the art, NLU is a branch of artificial intelligence (AI) that uses computer software to understand verbal inputs provided by a user (e.g., clinician 38). NLU may directly enable human-computer interaction (HCI), wherein the understanding of natural human language may enable computers to understand human-provided commands (without the formalized syntax of computer languages) and further enable these computers to respond to the human in their own language. The field of NLU is an important and challenging subset of natural language processing (NLP), as NLU is tasked with communicating with untrained individuals and understanding their intent. Accordingly, NLU goes beyond understanding words and actually interprets the meaning of such words. NLU may use algorithms to reduce human speech into a structured ontology, fleshing out such things as intent, timing, locations and sentiments.

As is known in the art, natural language processing (NLP) is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology may then accurately extract information and insights contained in the documents as well as categorize and organize the documents themselves.

As is known in the art, artificial intelligence (AI) and/or machine learning (ML) is the study of computer algorithms that improve automatically through experience and by the use of data. Artificial intelligence and machine learning algorithms may build a model based on sample data (known as "training data") in order to make predictions or decisions without being explicitly programmed to do so. Artificial intelligence and machine learning algorithms may be used in a wide variety of applications, such as in medicine, email filtering, speech recognition, and computer vision, wherein it may be difficult or unfeasible to develop conventional algorithms to perform the needed tasks. Artificial intelligence and machine learning may involve computers discovering how they can perform tasks without being explicitly programmed to do so (e.g., where computers learn from sample data (known as "training data") how to carry out certain tasks.

As is known in the art, a machine learning system or model may generally include an algorithm (or combination of algorithms) that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

Once the platform-useable command is generated, communication process 10 may provide 206 the platform-useable command (e.g., platform-useable command 60) to at least a portion of the plurality of disparate platforms (e.g., disparate platforms 46, 48, 50, 52, 54, 56) via the communication computing system (e.g., communication computing system 12).

For the following example, assume that monitor 150 is a diagnostic healthcare display (e.g., such as a healthcare display offered by Barco™). Accordingly, monitor 150 may be controllable by illumination platform 54, which may be executed on workstation computing system 36. Through the use of illumination platform 54, clinician 38 may control various aspects of monitor 150, such as adjusting the brightness, adjusting the contrast, and enabling resolution enhancing features. In order to enable such control of monitor 150, monitor 150 may execute illumination application 166, which may be configured to process commands received from illumination platform 54.

For the following example, assume that verbal information/command 44 provided by clinician 38 is "Hey Monitor . . . Turn on Illuminate", which instructs monitor 150 to turn on a resolution enhancing feature called "Illuminate". Accordingly, communication process 10 (via conversation AI platform) may process 202 verbal information/command 44 (e.g., "Hey Monitor . . . Turn on Illuminate") to generate a platform-useable command (e.g., platform-useable command 60), wherein an example of platform-useable command 60 may include "Monitor: Illuminate Status=1".

When providing 206 the platform-useable command (e.g., platform-useable command 60) to at least a portion of the plurality of disparate platforms (e.g., disparate platforms 46, 48, 50, 52, 54, 56) via the communication computing system (e.g., communication computing system 12), communication process 10 may:

> receive 208 the platform-useable command (e.g., platform-useable command 60) on the communication computing system (e.g., communication computing system 12); and
>
> broadcast 210 the platform-useable command (e.g., platform-useable command 60) to at least a portion of the plurality of disparate platforms (e.g., disparate platforms 46, 48, 50, 52, 54, 56).

As discussed above, communication process 10 may enable 200 clinician 38 to issue verbal information/command 44 (e.g., "Hey Monitor . . . Turn on Illuminate"), which may be processed 204 by conversational AI platform 52 (which is executed on report computing system 34) to generate platform-useable command 60 (e.g., Monitor: Illuminate Status=1). Conversational AI platform 52 may then provide platform-useable command 60 to communication computing system 12.

Once the platform-useable command (e.g., platform-useable command 60) is received 208 on the communication computing system (e.g., communication computing system 12), the communication computing system (e.g., communication computing system 12) may broadcast 210 the platform-useable command (e.g., platform-useable command 60) to a portion of the plurality of disparate platforms (e.g., illumination platform 54).

Once broadcast 210, communication process 10 may receive 212 the platform-useable command (e.g., command 46) on at least one of the plurality of disparate platforms (e.g., computing systems 12, 28, 30, 32, 34). For example, communication process 10 may receive 212 platform-useable command 60 on illumination platform 54 (which is executed on workstation computing system 36). Communication process 10 may then process 214 platform-useable command 60 on illumination platform 54, wherein illumination platform 54 may provide the necessary commands to illumination application 166 (which is executed on monitor 150) so that the Illuminate functionality may be turned on.

In the event that the platform-useable command 60 has some ambiguity, illumination application 166/illumination platform 54 (via communication computing system 12→conversational AI platform 52) may make an inquiry (possibly verbally) to clarify the ambiguity. For example, if Illuminate has three brightness levels, illumination application 166/illumination platform 54 may verbally ask clinician 38 "What level of brightness would you prefer?"

Figure 5:
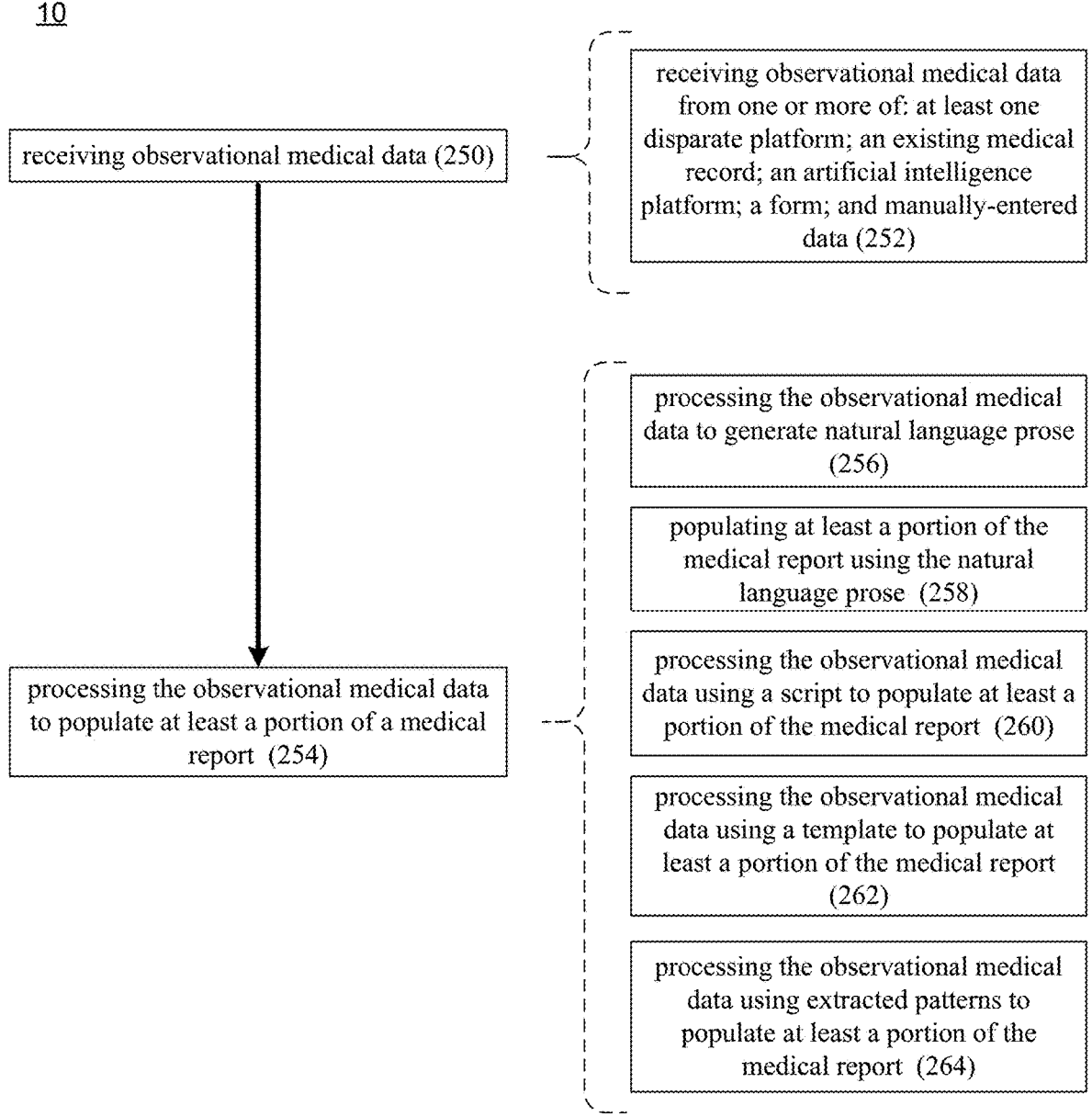
FIG. 5 is a flow chart of another implementation of the communication process of FIG. 1 according to an implementation of this disclosure.

Referring also to FIG. 5, communication process 10 may receive 250 observational medical data (e.g., data 58). When receiving 250 this observational medical data (e.g., data 58), communication process 10 may receive 252 observational medical data (e.g., data 58) from one or more of:

> At Least One Disparate Platform: For example, communication process 10 may be configured to obtain observational medical data (e.g., data 58) from any of the disparate platform (e.g., disparate platforms 46, 48, 50, 52, 54, 56) that are accessible to communication process 10.
>
> An Existing Medical Record: For example, communication process 10 may be configured to process existing medical records (e.g., medical records 72) available via medical record platform 50 to extract observational medical data (e.g., data 58).
>
> An Existing Medical Report: For example, communication process 10 may be configured to process existing medical reports (e.g., medical reports 74) available via medical report platform 48 to extract observational medical data (e.g., data 58).
>
> An Artificial Intelligence Platform: For example, communication process 10 may be configured to utilize an artificial intelligence platform (e.g., medical analysis platform 56) to process (for example) existing medical records (e.g., medical records 72), existing medical reports (e.g., medical reports 74), existing medical forms (e.g., handwritten note 76) and existing medical recordings (e.g., voice recording 78) to extract observational medical data (e.g., data 58).
>
> Manually-Entered Data: For example, communication process 10 may be configured to receive observational medical data (e.g., data 58) manually entered by clinician 38 via e.g., audio input device 42, a keyboard (not shown) and/or a pointing device (not shown) coupled to workstation computing system 36.

Accordingly and when utilizing observational medical data (e.g., data 58) to populate a medical report (e.g., medical report 40), this observational medical data (e.g., data 58) may be obtained from basically any source. Further, this observational data (e.g., data 58) need not be provided by a human being (e.g., clinician 38) and may be provided without human intervention via e.g., artificial intelligence.

Once received 250, communication process 10 may process 254 the observational medical data (e.g., data 58) to populate at least a portion of a medical report (e.g., medical report 40).

When processing 254 the observational medical data (e.g., data 58) to populate at least a portion of a medical report (e.g., medical report 40), communication process 10 may:

> process 256 the observational medical data (e.g., data 58) to generate natural language prose 80 using e.g., conversational AI platform 52; and
>
> populate 258 at least a portion of the medical report (e.g., medical report 40) using natural language prose 80.

Continuing with the above-stated example, the observational data (e.g., data 58) for patient John Smith identifies the following:

PATIENT: John Smith;
TYPE: Growth;
LOCATION: Lower Quadrant of Left Lung; and
SIZE: 5.1 Centimeters.

Accordingly and upon receiving 250 observational medical data 58 (e.g., John Smith, Growth, Lower Quadrant of Left Lung, 5.1 Centimeters), communication process 10 may process 256 the observational medical data (e.g., data 58) to generate natural language prose 80 using e.g., conversational AI platform 52 executed on report computing system 34. For example, communication process 10 may process 256 observational medical data 58 (e.g., John Smith, Growth, Lower Quadrant of Left Lung, 5.1 Centimeters) to generate natural language prose 80, an example of which may include but is not limited to "Patient John Smith has a growth in the lower quadrant of left lung that measures 5.1 centimeters". Once natural language prose 80 is generated, communication process 10 may populate 258 at least a portion of the medical report (e.g., medical report 40) using natural language prose 80. For example, communication process 10 may populate 258 field 164 within medical report 40 to state that "Patient John Smith has a growth in the lower quadrant of left lung that measures 5.1 centimeters"

Additionally/alternatively and when processing 254 the observational medical data (e.g., data 58) to populate at least a portion of a medical report (e.g., medical report 40), communication process 10 may process 260 the observational medical data (e.g., data 58) using a script (e.g., script 82) to populate at least a portion of the medical report (e.g., medical report 40). For example, script 82 may be defined by e.g., clinician 38 and may generally function as an if/then statement that may be used when mapping data into the appropriate fields within medical report 40. Additionally,/alternatively, script 82 may be generated using AI functionality available via medical analysis platform 56. For example, script 82 may define keywords and/or standardized medical codes that are associable with specific fields within a medical report. For example, the keyword:

"renal" may be associable with the "Kidneys" field within medical report 40;

"pneumonia" may be associable with the "Lungs" field within medical report 40; and "aorta" may be associable with the "Heart" field within medical report 40.

Additionally, script 82 may be utilized to quantify an entity. For example, script 82 say that:

if a growth 6.00 cm or greater, it is a large growth;

if a growth is 3.00-5.99 cm, it is a medium growth; and if a growth is less than 2.99 cm, it is a small growth.

Additionally/alternatively and when processing 254 the observational medical data (e.g., data 58) to populate at least a portion of a medical report (e.g., medical report 40), communication process 10 may process 262 the observational medical data (e.g., data 58) using a template (e.g., template 84) to populate at least a portion of the medical report (e.g., medical report 40). For example, template 84 may be manually-defined by e.g., clinician 38 and may generally provide the structure for the language that is used to populate medical report 40.

In the example discussed above, communication process 10 may populate process medical report 40 with "Patient John Smith has a growth in the lower quadrant of left lung that measures 5.1 centimeters". As discussed above, the observational data (e.g., data 58) included within this statement is "_____ John Smith _____ growth _____ lower quadrant of left lung _____ 5.1 centimeters". Accordingly, an example of template 84 (which may define the structure for this statement) may be "Patient _____ has a _____ in the _____ that measures _____".

While template 84 is described above as being defined by a human being (e.g., clinician 38), other configurations are possible and are considered to be within the scope of this disclosure. For example, template 84 may be generated via artificial intelligence.

Accordingly and when processing 254 the observational medical data (e.g., data 58) to populate at least a portion of a medical report (e.g., medical report 40), communication process 10 may process 264 the observational medical data (e.g., data 58) using extracted patterns (e.g., extracted patterns 86) to populate at least a portion of the medical report (e.g., medical report 40), wherein these extracted patterns (e.g., extracted patterns 86) may be used to generate one or more templates (e.g., template 84).

For example, these extracted patterns (e.g., extracted patterns 86) may be generated using artificial intelligence (via e.g., medical analysis platform 56) to process a plurality of previously-generated medical reports (e.g., medical reports 74). For example, communication process 10 may utilize medical analysis platform 56 to analyze medical reports 74 to identify patterns within these medical reports.

As is known in the art, pattern recognition is the process of recognizing patterns using a machine learning algorithm. Pattern recognition may be defined as the classification of data based on knowledge already gained or on statistical information extracted from patterns and/or their representation. Pattern recognition is generally the ability to detect arrangements of characteristics or data that yield information about a given system or data set. In a technological context, a recognized patterns might be recurring sequences of data over time that may be used to predict trends, particular configurations of features in images that identify objects, frequent combinations of words and phrases for natural language processing (NLP), or particular clusters of behaviors on a network that could indicate an attack.

Accordingly, communication process 10 may utilize medical analysis platform 56 to analyze previously-generated medical reports 74 to identify patterns (e.g., extracted patterns 86) within these previously-generated medical reports 74, wherein these extracted patterns (e.g., extracted patterns 86) may be used to generate one or more templates (e.g., template 84). For example and upon communication process 10 utilizing medical analysis platform 56 to analyze previously-generated medical reports 74, an extracted pattern (e.g., extracted pattern 86) may be identified, wherein entities are typically reported as follows: "Patient _____ has a _____ in the _____ that measures _____". Accordingly, this extracted pattern may be utilized to generate one or more templates (e.g., template 84).

As will be discussed below in greater detail, these extracted patterns (e.g., extracted patterns 86) may be used by communication process 10 to define options for clinician 38 (e.g., a radiologist, a cardiologist or a pathologist) as to e.g., which field within medical report 40 a particular statement (e.g., "Patient John Smith has a growth in the lower quadrant of left lung that measures 5.1 centimeters") should be placed.

Figure 6:
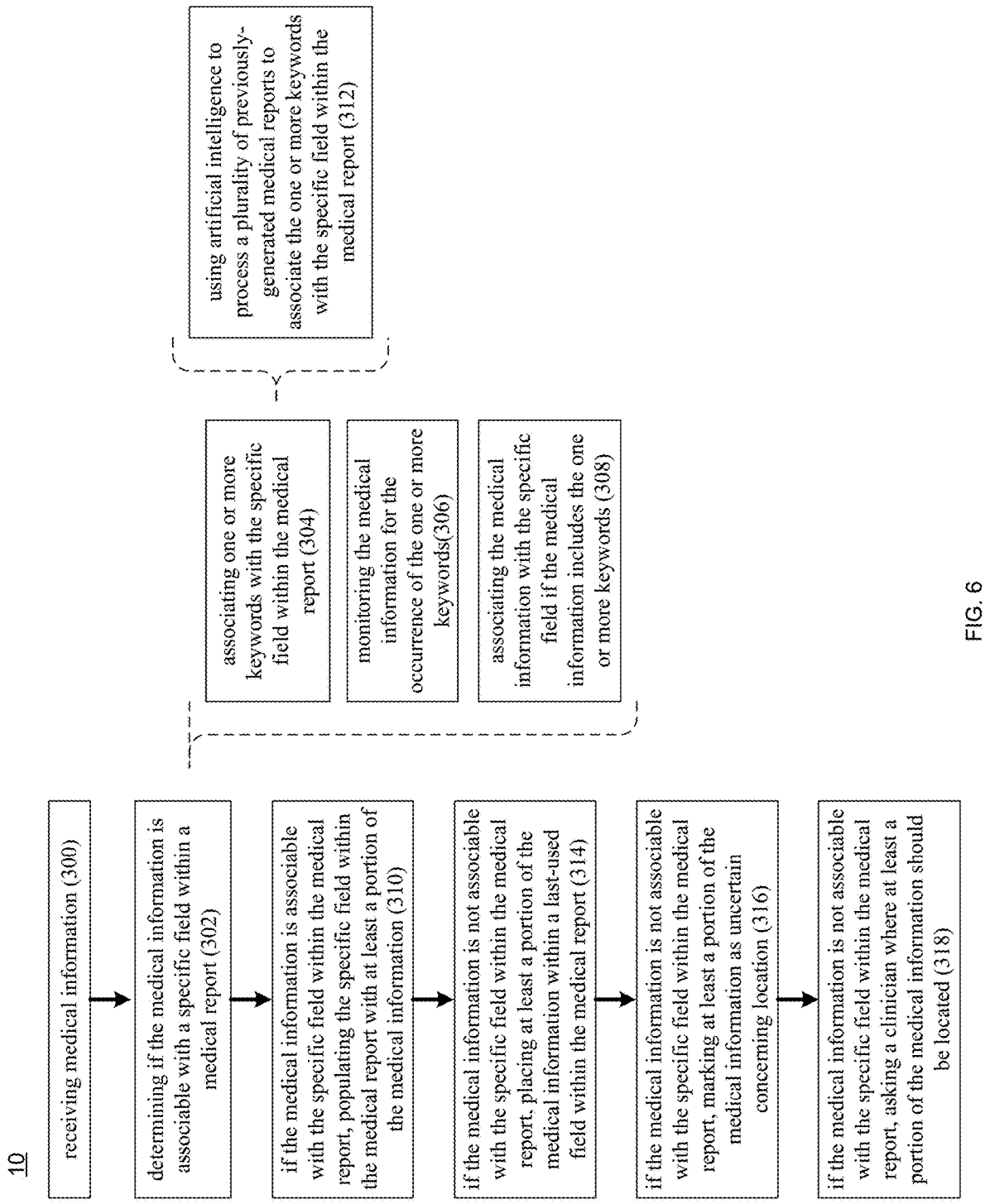
FIG. 6 is a flow chart of another implementation of the communication process of FIG. 1 according to an implementation of this disclosure.

Referring also to FIG. 6 and as discussed above, communication process 10 may receive 300 medical information (e.g., data 20). As also discussed above, communication process 10 may utilize this medical information (e.g., data 20) to populate medical reports (e.g., medical report 40).

The medical information (e.g., data 20) may include one or more of:

medical information (e.g., data 20) dictated by clinician 38 (e.g., a radiologist, a cardiologist or a pathologist). For example, clinician 38 may dictate verbal information via e.g., audio input device 42 coupled to workstation computing system 36. This verbal information may be processed via artificial intelligence platform (e.g., conversational AI platform and/or medical analysis platform 56).

medical information (e.g., data 20) obtained from at least one disparate platform (e.g., disparate platforms 46, 48, 50, 52, 54, 56).

medical information (e.g., data 20) obtained from an existing medical record (e.g., medical records 72).

medical information (e.g., data 20) obtained from an artificial intelligence platform (e.g., medical analysis platform 56).

medical information (e.g., data 20) obtained from a form (e.g., handwritten note 76).

medical information (e.g., data 20) that is manually entered by clinician 38 via e.g., a keyboard (not shown) and/or a pointing device (not shown) coupled to workstation computing system 36.

However, in order for communication process 10 to properly utilize such medical information (e.g., data 20), communication process 10 will need to know the appropriate field into which to place medical information (e.g., data 20).

Accordingly, communication process 10 may determine 302 if the medical information (e.g., data 20) is associable with a specific field (e.g., field 164) within a medical report (e.g., medical report 40).

When determining 302 if the medical information (e.g., data 20) is associable with a specific field (e.g., field 164) within a medical report (e.g., medical report 40), communication process 10 may:

- associate 304 one or more keywords and/or standardized medical codes with the specific field (e.g., field 164) within the medical report (e.g., medical report 40);
- monitor 306 the medical information (e.g., data 20) for the occurrence of the one or more keywords and/or standardized medical codes; and
- associate 308 the medical information (e.g., data 20) with the specific field if the medical information (e.g., data 20) includes the one or more keywords and/or standardized medical codes.

As discussed above, script 82 may be defined by e.g., clinician 38 and may generally function as an if/then statement that may be used when mapping data into the appropriate fields within medical report 40. Additionally,/alternatively, script 82 may be generated using AI functionality available via medical analysis platform 56. For example, script 82 may define keywords and/or standardized medical codes that are associable with specific fields within a medical report. For example, the keyword:

- "renal" may be associable with the "Kidneys" field within medical report 40;
- "pneumonia" may be associable with the "Lungs" field within medical report 40; and
- "aorta" may be associable with the "Heart" field within medical report 40.

Accordingly and when determining 302 if the medical information (e.g., data 20) is associable with a specific field (e.g., field 164) within a medical report (e.g., medical report 40), communication process 10 may monitor 306 the medical information (e.g., data 20) for the occurrence of the one or more keywords and/or standardized medical codes.

Therefore:

- if the medical information (e.g., data 20) includes the keyword "renal", the medical information (e.g., data 20) may be associated 308 with the "Kidneys" field (e.g., field 168) within medical report 40;
- if the medical information (e.g., data 20) includes the keyword "pneumonia", the medical information (e.g., data 20) may be associated 308 with the "Lungs" field (e.g., field 164) within medical report 40; and
- if the medical information (e.g., data 20) includes the keyword "aorta", the medical information (e.g., data 20) may be associated 308 with the "Heart" field (e.g., field 170) within medical report 40.

If the medical information (e.g., data 20) is associable with the specific field (e.g., one of fields 164, 168, 170) within the medical report (e.g., medical report 40), communication process 10 may populate 310 the specific field (e.g., one of fields 164, 168, 170) within the medical report (e.g., medical report 40) with at least a portion of the medical information (e.g., data 20).

When associating 304 one or more keywords and/or standardized medical codes with the specific field (e.g., one of fields 164, 168, 170) within the medical report (e.g., medical report 40), communication process 10 may use 312 artificial intelligence (e.g., medical analysis platform 56) to process a plurality of previously-generated medical reports (e.g., medical report 40) to associate the one or more keywords and/or standardized medical codes with the specific field (e.g., one of fields 164, 168, 170) within the medical report (e.g., medical report 40).

As discussed above, pattern recognition is the process of recognizing patterns using a machine learning algorithm. Accordingly, communication process 10 may utilize medical analysis platform 56 to analyze previously-generated medical reports 74 to identify patterns (e.g., extracted patterns 86) within these previously-generated medical reports 74. These extracted patterns (e.g., extracted patterns 86) may be used to identify the above-described keywords and/or standardized medical codes.

For example, communication process 10 may use 312 artificial intelligence (e.g., medical analysis platform 56) to determine that:

- 96.3% of the time that "renal" is mentioned, it is in the "Kidneys" field (e.g., field 168) within medical report 40;
- 98.9% of the time that "pneumonia" is mentioned, it is in the "Lungs" field (e.g., field 164) within medical report 40; and
- 97.4% of the time that "aorta" is mentioned, it is in the "Heart" field (e.g., field 170) within medical report 40.

Accordingly, communication process 10 may associate 304:

- "renal" with the "Kidneys" field (e.g., field 168) within medical report 40;
- "pneumonia" with the "Lungs" field (e.g., field 164) within medical report 40; and
- "aorta" with the "Heart" field (e.g., field 170) within medical report 40.

If the medical information (e.g., data 20) is not associable with the specific field (e.g., one of fields 164, 168, 170) within the medical report (e.g., medical report 40), communication process 10 may place 314 at least a portion of the medical information (e.g., data 20) within a last-used field within the medical report (e.g., medical report 40). For example, if clinician 38 was dictating (via e.g., audio input device 42) medical information (e.g., data 20) that included the keyword "renal", that medical information (e.g., data 20) would be placed within field 168 (for the reasons discussed above). If clinician 38 paused for a bit and then dictated "So I recommend the appropriate treatment", this medical information (e.g., data 20) does not include any keywords and/or standardized medical codes. However, being it was dictated following information that was associable with field 168, communication process 10 may place 314 at least a portion of the medical information (e.g., "So I recommend the appropriate treatment") within a last-used field (e.g., field 168) within the medical report (e.g., medical report 40).

Additionally/alternatively, if the medical information (e.g., data 20) is not associable with the specific field (e.g., one of fields 164, 168, 170) within the medical report (e.g., medical report 40), communication process 10 may mark 316 at least a portion of the medical information (e.g., data 20) as uncertain concerning location. For example, communication process 10 may insert a parenthetical (e.g., PLEASE CONFIRM LOCATION) prior to or after the information in question to mark 316 the location of the information as uncertain.

Further and if the medical information (e.g., data 20) is not associable with the specific field (e.g., one of fields 164, 168, 170) within the medical report (e.g., medical report 40), communication process 10 may ask 318 clinician 38 (e.g., a radiologist, a cardiologist or a pathologist) where at least a portion of the medical information (e.g., data 20) should be located. For example, communication process 10 may render popup window 172 that asks 318 clinician 38 to confirm the location of the information in question.

Gaze Detection

Figure 7:
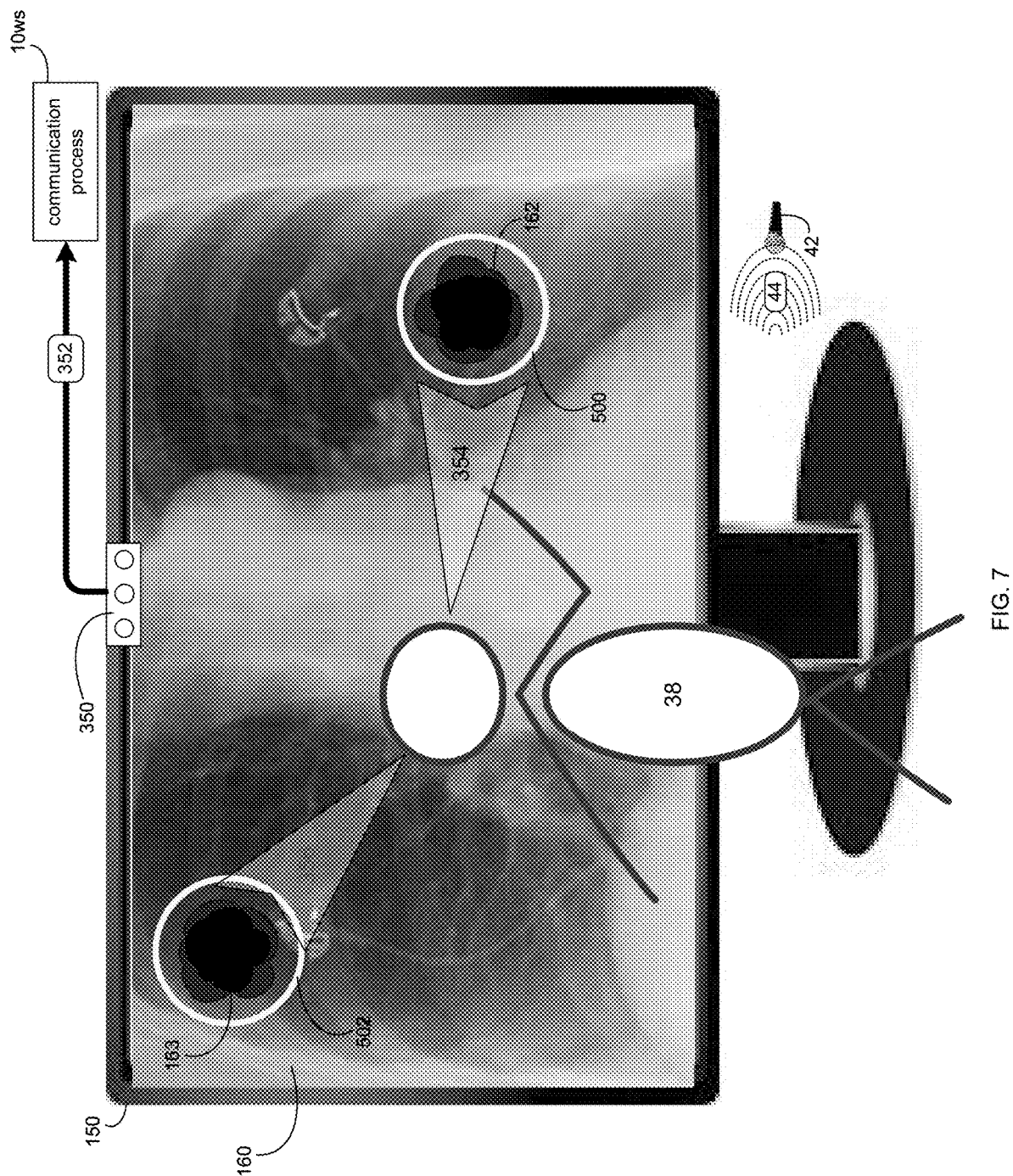
FIG. 7 is another diagrammatic view of a workstation computing system executing the communication process of FIG. 1.

Referring also to FIG. 7, assume that clinician 38 (e.g., a radiologist, a cardiologist or a pathologist) is reviewing chest x-ray image 160 (e.g., data 20) of a patient (e.g., patient John Smith) using medical image platform portion 156 being executed on workstation computing system 36. As discussed above, chest x-ray image 160 includes a growth (e.g., growth 162) that is being reviewed by clinician 38. Further, assume for this example that chest x-ray image 160 also includes a second growth (e.g., growth 163) that is also being reviewed by clinician 38.

Assume as discussed above that that clinician 38 is providing verbal commentary (e.g., verbal information/command 44) concerning each of these two growths (e.g., growths 162, 163), wherein such verbal commentary (e.g., verbal information/command 44) may be utilized for medical report creation. Unfortunately, it is foreseeable that clinician 38 may provide verbal commentary (e.g., verbal information/command 44) that is location ambiguous. For example, assume that clinician 38 provides the following verbal commentary (e.g., verbal information/command 44) concerning growths 162, 163:

"There is a first growth that appears to be concerning due to its location and the high likelihood of penetrating deep into the lung tissue. Moving on to the second growth, this particular growth is much less concerning due to its overall shape and non-critical location."

As there is no location information provided with respect to each of these growths, it is unclear if the "first growth" in the verbal commentary (e.g., verbal information/command 44) uttered by clinician 38 is growth 162 or growth 163. Similarly, as there is no location information associated with the "second growth" in the verbal commentary (e.g., verbal information/command 44) uttered by clinician 38, it is also unclear if this "second growth" is growth 162 or growth 163.

Accordingly, and in order to eliminate such location ambiguity, gaze detection device 350 may be utilized to generate gaze information 352 that is provided to communication process 10ws, which is executed on workstation computing system 36. Gaze detection device 350 may include one or more camera assemblies to identify the point of gaze of the user (e.g., clinician 38). As discussed above, clinician 38 may use medical image platform portion 156 executed on workstation computing system 36 to review chest x-ray image 160 (e.g., data 20) of a patient (e.g., patient John Smith).

Accordingly, such audio-based content (e.g., verbal information/command 44) and gaze information (e.g., gaze information 352) may be generated during a diagnostic session (e.g., when clinician 38 is reviewing chest x-ray image 160 of patient John Smith).

As is known in the art, gaze detection refers to the process of measuring where a person is looking (e.g., their point of gaze). These measurements may be carried out by an eye tracker (e.g., gaze detection device 350) that records the position of the eyes and the movements they make. Near-infrared light may be directed towards the center of the eyes (pupil), causing detectable reflections in both the pupil and the cornea. These reflections (i.e., the vector between the cornea and the pupil) may be tracked by an infrared camera, resulting in the optical tracking of corneal reflections (known as pupil center corneal reflection (PCCR)).

Figure 8:
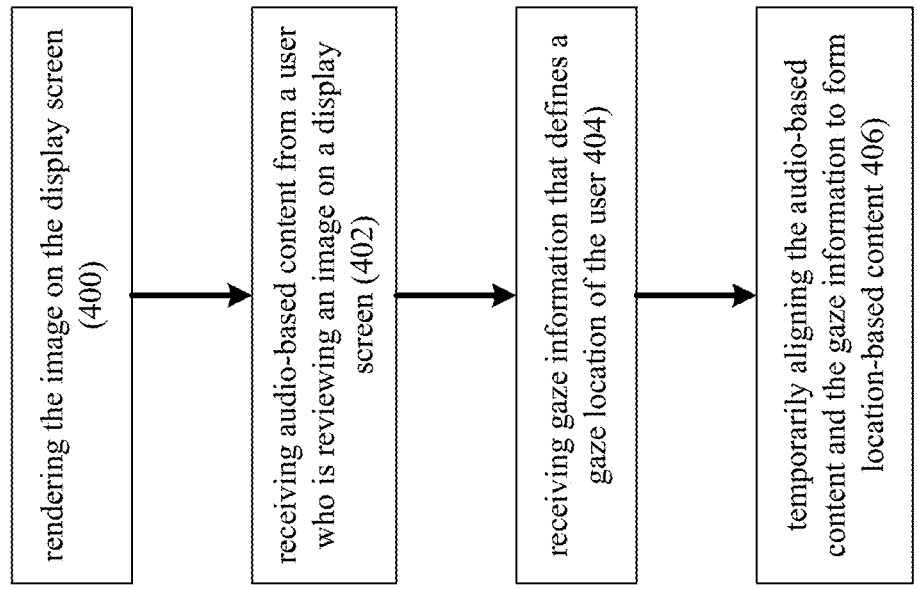
FIG. 8 is a flow chart of another implementation of the communication process of FIG. 1 according to an implementation of this disclosure.

Accordingly and referring also to FIG. 8, communication process 10 may render 400 an image on the display screen (e.g., monitor 150). Continuing with the above-stated example, this image may be a medical image (e.g., x-ray image 160).

Communication process 10 may receive 402 audio-based content (e.g., verbal information/command 44) from a user (e.g., clinician 38) who is reviewing an image (e.g., x-ray image 160) on a display screen (e.g., monitor 150). Specifically and as discussed above, clinician 38 (e.g., a radiologist, a cardiologist or a pathologist) may review chest x-ray image 160 (e.g., data 20) of patient John Smith using medical image platform portion 156 being executed on workstation computing system 36, wherein chest x-ray image 160 may show two growths (e.g., growths 162, 163). The audio-based content (e.g., verbal information/command 44) may be descriptive content that describes a portion of the medical image (e.g., x-ray image 160).

Continuing with the above-stated example, this audio-based content (e.g., verbal information/command 44) may include:

"There is a first growth that appears to be concerning due to its location and the high likelihood of penetrating deep into the lung tissue."; and "Moving on to the second growth, this particular growth is much less concerning due to its overall shape and non-critical location."

As neither of these two portions of audio-based content (e.g., verbal information/command 44) have location information associated with them, communication process 10 may receive 404 gaze information (e.g., gaze information 352) that defines a gaze location (e.g., gaze location 354 or gaze location 356) of the user (e.g., clinician 238). Specifically, this gaze information (e.g., gaze information 352) may define a gaze location (e.g., gaze location 354 or gaze location 356) of the user (e.g., clinician 238) with respect to a portion of the image (e.g., chest x-ray image 160) on a display screen (e.g., monitor 150). For example, assume that during a first portion of time, communication process 10 receives 404 gaze information (e.g., gaze information 352) that defines a gaze location (e.g., gaze location 354) of the user (e.g., clinician 238), while during a second portion of time, communication process 10 receives 404 gaze information (e.g., gaze information 352) that defines a gaze location (e.g., gaze location 356) of the user (e.g., clinician 238). Gaze location 354 and/or gaze location 356 may be defined in various ways, an example of which may include but is not limited to defining e.g., the center of gaze coordinates for the user (e.g., clinician 238) and a viewing radius with respect to the center of gaze coordinates.

Communication process 10 may temporally align 406 the audio-based content (e.g., verbal information/command 44) and the gaze information (e.g., gaze information 352) to form location-based content (e.g., location-based content 358). For example, assume that it took 40 seconds for clinician 38 to say "There is a first growth that appears to be concerning due to its location and the high likelihood of penetrating deep into the lung tissue. Moving on to the second growth, this particular growth is much less concerning due to its overall shape and non-critical location.".

Further and with respect to the audio-based content (e.g., verbal information/command 44), assume that it took 15 seconds for clinician 38 to say "There is a first growth that appears to be concerning due to its location and the high likelihood of penetrating deep into the lung tissue." This was then followed by a 10 second pause, and then it took 15 seconds for clinician 38 to say "Moving on to the second growth, this particular growth is much less concerning due to its overall shape and non-critical location.".

Additionally and with respect to the gaze information (e.g., gaze information 352), assume during the 15 seconds in which clinician 38 was saying "There is a first growth that appears to be concerning due to its location and the high likelihood of penetrating deep into the lung tissue", gaze information 352 was indicating that the clinician was looking in the direction of gaze location 354. Then during the 10 second pause, clinician 38 switched from gaze location 354 to gaze location 356 (while e.g., staring offscreen for a few seconds to refocus their eyes). And then during the 15 seconds in which clinician 38 was saying "Moving on to the second growth, this particular growth is much less concerning due to its overall shape and non-critical location.", gaze information 352 was indicating that clinician 38 was looking in the direction of gaze location 356.

Accordingly, location-based content (e.g., location-based content 358) may associate "There is a first growth that appears to be concerning due to its location and the high likelihood of penetrating deep into the lung tissue" with growth 162 that is in the lower portion of the left lung of patient John Smith (as that is what clinician 38 was looking at with gaze location 354). Further, location-based content (e.g., location-based content 358) may associate "Moving on to the second growth, this particular growth is much less concerning due to its overall shape and non-critical location" with growth 163 that is in the upper portion of the right lung of patient John Smith (as that is what clinician 38 was looking at with gaze location 356).

Communication process 10 may use this location-based content (e.g., location-based content 358) to populate a medical report (e.g., medical report 40) in the manner defined above. Accordingly, the "Lungs" field (e.g., field 164) within medical report 40 may be populated with:
"There is a first growth [IN THE LOWER PORTION OF THE LEFT LUNG] that appears to be concerning due to its location and the high likelihood of penetrating deep into the lung tissue."; and
"Moving on to the second growth, this particular growth [IN THE UPPER PORTION OF THE RIGHT LUNG] is much less concerning due to its overall shape and non-critical location."

While the audio-based content (e.g., verbal information/command 44) and the gaze information 352 is described above as being utilized for populating a medical report (e.g., medical report 40), this is for illustrative purposes only and is not intended to be limitation of this disclosure, as other configurations are possible and are considered to be within the scope of this disclosure. For example, the audio-based content (e.g., verbal information/command 44) and the gaze information 352 may be generated during an AI model training session and may be utilized to train an AI model (e.g., AI model 88).

As discussed above, an artificial intelligence platform (e.g., medical analysis platform 56) may be configured to process (for example) existing medical records (e.g., medical records 72), existing medical reports (e.g., medical reports 74), existing medical forms (e.g., handwritten note 76) and existing medical recordings (e.g., voice recording 78) to extract observational medical data (e.g., data 58). As is known in the art, such an artificial intelligence platform may utilize AI models (e.g., AI model 88) to e.g., make predictions, identify problems, define best practices, etc. Accordingly, the artificial intelligence platform (e.g., medical analysis platform 56) may be configured to preprocess (for example) chest x-ray image 160 of patient John Smith to identify e.g., any potential growths. Feedback may then be provided to the artificial intelligence platform (e.g., medical analysis platform 56) so that the AI model (e.g., AI model 88) may be further refined to enhance its accuracy.

As discussed above, clinician 38 deems ". . . first growth [IN THE LOWER PORTION OF THE LEFT LUNG] . . . to be concerning due to its location and the high likelihood of penetrating deep into the lung tissue.", while deeming " . . . the second growth . . . [IN THE UPPER PORTION OF THE RIGHT LUNG] . . . much less concerning due to its overall shape and non-critical location.". This location-based content (e.g., location-based content 358) or some portion thereof may be provided to artificial intelligence platform (e.g., medical analysis platform 56) as feedback to train/refine AI model 88.

Accordingly (and in a greatly simplified fashion), if medical analysis platform 56 deemed both of growths 162, 163 to be concerning, the artificial intelligence platform (e.g., medical analysis platform 56) would have an accuracy of 50% (as growth 163 is not concerning according to clinician 38). Therefore, location-based content (e.g., location-based content 358) or some portion thereof may be utilized to slightly revise AI model 88.

Further (and in a greatly simplified fashion), if medical analysis platform 56 deemed both of growths 162, 163 to be non-concerning, the artificial intelligence platform (e.g., medical analysis platform 56) would have an accuracy of 50% (as growth 162 is concerning according to clinician 38). Therefore, location-based content (e.g., location-based content 358) or some portion thereof may be utilized to slightly revise AI model 88.

Additionally (and in a greatly simplified fashion), if medical analysis platform 56 deemed growths 162 to be non-concerning and growth 163 to be concerning, the artificial intelligence platform (e.g., medical analysis platform 56) would have an accuracy of 0% (as growth 162 is concerning and growth 163 is not concerning according to clinician 38). Therefore, location-based content (e.g., location-based content 358) or some portion thereof may be utilized to highly revise AI model 88.

Further (and in a greatly simplified fashion), if medical analysis platform 56 deemed growths 162 to be concerning and growth 163 to be non-concerning, the artificial intelligence platform (e.g., medical analysis platform 56) would have an accuracy of 100% (as growth 162 is concerning and growth 163 is not concerning according to clinician 38). Therefore, location-based content (e.g., location-based content 358) or some portion thereof may be utilized to reinforce/reaffirm the accuracy of AI model 88.

While the audio-based content (e.g., verbal information/command 44) and the gaze information 352 is described above as being utilized for populating a medical report (e.g., medical report 40) and/or training an AI model (e.g., AI model 88), this is for illustrative purposes only and is not intended to be limitation of this disclosure, as other configurations are possible and are considered to be within the scope of this disclosure. For example, the audio-based content (e.g., verbal information/command 44) and the gaze information 352 may be generated during a telehealth session.

Figure 9:
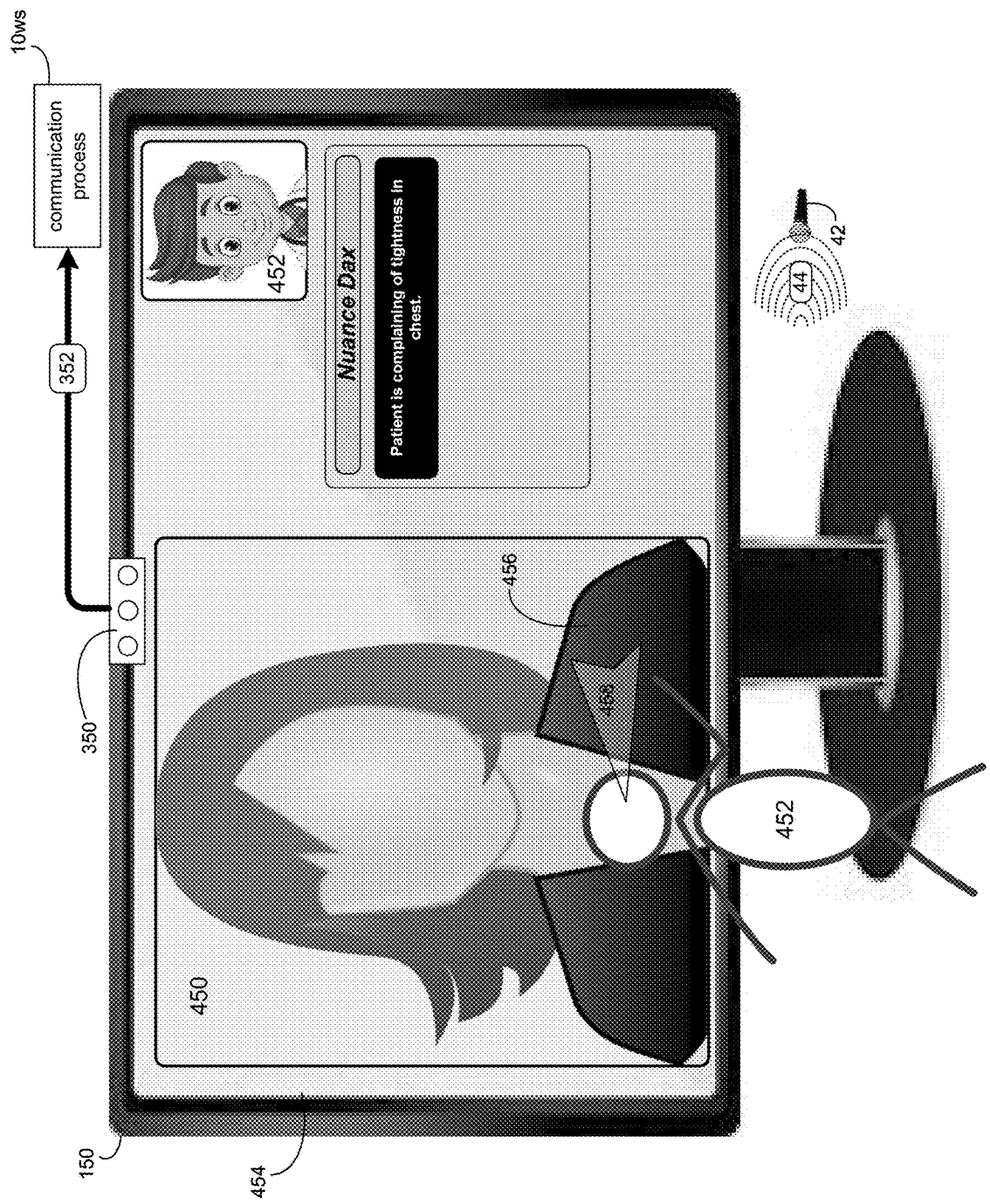
FIG. 9 is another diagrammatic view of a workstation computing system executing the communication process of FIG. 1.

Referring also to FIG. 9, assume that patient 450 is meeting with doctor 452 during a telehealth visit. As is known in the art, telehealth is the distribution of health-related services and information via electronic information and telecommunication technologies. Telehealth medical encounters may allow long-distance patient and clinician contact, care, advice, reminders, education, intervention, monitoring, and remote admissions. Telemedicine may sometimes be used as a synonym, or may be used in a more limited sense to describe remote clinical services, such as diagnosis and monitoring. When rural settings, lack of transport, a lack of mobility, decreased funding, or a lack of staff restrict access to care; telehealth may bridge the gap, as well as provide: distance-learning, meetings, supervision, and presentations between practitioners; online information and health data management; and healthcare system integration. Telehealth may include two clinicians discussing a case over video conference; a robotic surgery occurring through remote access; physical therapy performed via digital monitoring instruments, live feed and application combinations; tests being forwarded between facilities for interpretation by a higher specialist; home monitoring through continuous sending of patient health data; client to practitioner online conference; or even videophone interpretation during a consult.

Accordingly and during such a telehealth visit, patient 450 and doctor 452 may be communicating via user interface 454. In this particular example, user interface 454 is a user interface rendered on monitor 150 coupled to a computer (e.g., workstation computing system 36) being utilized by doctor 452 to effectuate the telehealth visit.

Assume for this example that, during the telehealth visit, doctor 452 inquiries about shoulder 456 of patient 450. For example, doctor 452 may say "Does your shoulder hurt? I noticed that you are moving it weirdly", resulting in the generation of the audio-based content (e.g., verbal information/command 44). However, just like the earlier example concerning the discussions of growths 162, 163 within the lungs of patient John Smith, verbal information/command 44 uttered by doctor 452 ("Does your shoulder hurt? I noticed that you are moving it weirdly") does not include any location information, so it is unclear which shoulder (of patient 450) doctor 452 is referring to.

Again, the gaze information (e.g., gaze information 352) may define a gaze location (e.g., gaze location 458) of doctor 452 with respect to a portion of the image (e.g., the rendered image of patient 450) on a display screen (e.g., monitor 150). For example, gaze information 352 may define a gaze location (e.g., gaze location 458) of the user (e.g., doctor 452) that indicates that the "shoulder" referred to by doctor 452 when stating "Does your shoulder hurt? I noticed that you are moving it weirdly" is actually the left shoulder (e.g., shoulder 456) of patient 450, thus enabling the generation of location-based content 358 (as described above), which may be utilized to populate a medical report (e.g., medical report 40) in the manner defined above. For example, an appropriate field in a medical report (e.g., medical report 40) may be populated with:

"Does your [LEFT] shoulder hurt? I noticed that you are moving it weirdly"

While the audio-based content (e.g., verbal information/command 44) and the gaze information 352 is described above as being utilized for populating a medical report (e.g., medical report 40), training an AI model (e.g., AI model 88) and/or during a telehealth session, this is for illustrative purposes only and is not intended to be limitation of this disclosure, as other configurations are possible and are considered to be within the scope of this disclosure. For example, the audio-based content (e.g., verbal information/command 44) and the gaze information 352 may be utilized to enrich a medical image (e.g., chest x-ray image 160).

For example, the audio-based content (e.g., verbal information/command 44) and the gaze information 352 may be utilized to generate highlights (e.g., highlights 500, 502) within the medical image (e.g., chest x-ray image 160), wherein highlights 500, 502 are shown (in this example) to be contrasting rings placed around growths 162, 163. However, it is understood that different types of highlights may be generated and are considered to be within the scope of this disclosure. Such highlights (e.g., highlights 500, 502) may be utilized during subsequent review of medical image (e.g., chest x-ray image 160) by e.g., one or more medical professionals.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object-oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general-purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    receiving audio-based content from a user who is reviewing an image on a display screen;
    receiving gaze information that defines a first gaze location and a second gaze location of the user, wherein the gaze information defines a first gaze location of the user with respect to a first portion of the image on the display screen and a second gaze location of the user with respect to a second portion of the image on the display screen;
    temporally aligning the audio-based content and the gaze information to form location-based content associated with each of the first portion of the image on the display screen and the second portion of the image on the display screen; and
    associating the audio-based content from the user with each respective first and second portion of the image on the display screen defined by each respective first and second gaze location of the user.

2. The computer-implemented method of claim 1 further comprising:
    rendering the image on the display screen.

3. The computer-implemented method of claim 1 wherein the audio-based content and the gaze information are generated during a telehealth session.

4. The computer-implemented method of claim 1 wherein the audio-based content and the gaze information are generated during a diagnostic session.

5. The computer-implemented method of claim 1 wherein the audio-based content and the gaze information are generated during an AI model training session.

6. The computer-implemented method of claim 1 wherein the location-based content is utilized to populate a medical report.

7. The computer-implemented method of claim 1 wherein the location-based content is utilized to train an AI model.

8. The computer-implemented method of claim 1 wherein the location-based content is utilized to enrich a medical image.

9. The computer-implemented method of claim 8 wherein the audio-based content is descriptive content that describes a portion of the medical image.

10. A computer program product residing on a computer readable medium having a plurality of instructions stored thereon which, when executed by a processor, cause the processor to perform operations comprising:
- receiving audio-based content from a user who is reviewing an image on a display screen;
- receiving gaze information that defines a first gaze location and a second gaze location of the user, wherein the gaze information defines a first gaze location of the user with respect to a first portion of the image on the display screen and a second gaze location of the user with respect to a second portion of the image on the display screen;
- temporally aligning the audio-based content and the gaze information to form location-based content associated with each of the first portion of the image on the display screen and the second portion of the image on the display screen; and
- associating the audio-based content from the user with each respective first and second portion of the image on the display screen defined by each respective first and second gaze location of the user.

11. The computer-implemented method of claim 10 further comprising:
- rendering the image on the display screen.

12. The computer-implemented method of claim 10 wherein the audio-based content and the gaze information are generated during a telehealth session.

13. The computer-implemented method of claim 10 wherein the audio-based content and the gaze information are generated during a diagnostic session.

14. The computer-implemented method of claim 10 wherein the audio-based content and the gaze information are generated during an AI model training session.

15. The computer-implemented method of claim 10 wherein the location-based content is utilized to populate a medical report.

16. The computer-implemented method of claim 10 wherein the location-based content is utilized to train an AI model.

17. The computer-implemented method of claim 10 wherein the location-based content is utilized to enrich a medical image.

18. The computer-implemented method of claim 17 wherein the audio-based content is descriptive content that describes a portion of the medical image.

19. A computing system including a processor and memory configured to perform operations comprising:
- receiving audio-based content from a user who is reviewing an image on a display screen;
- receiving gaze information that defines a first gaze location and a second gaze location of the user, wherein the gaze information defines a first gaze location of the user with respect to a first portion of the image on the display screen and a second gaze location of the user with respect to a second portion of the image on the display screen;
- temporally aligning the audio-based content and the gaze information to form location-based content associated with each of the first portion of the image on the display screen and the second portion of the image on the display screen; and
- associating the audio-based content from the user with each respective first and second portion of the image on the display screen defined by each respective first and second gaze location of the user.

20. The computer-implemented method of claim 19 further comprising:
- rendering the image on the display screen.

21. The computer-implemented method of claim 19 wherein the audio-based content and the gaze information are generated during a telehealth session.

22. The computer-implemented method of claim 19 wherein the audio-based content and the gaze information are generated during a diagnostic session.

23. The computer-implemented method of claim 19 wherein the audio-based content and the gaze information are generated during an AI model training session.

24. The computer-implemented method of claim 19 wherein the location-based content is utilized to populate a medical report.

25. The computer-implemented method of claim 19 wherein the location-based content is utilized to train an AI model.

26. The computer-implemented method of claim 19 wherein the location-based content is utilized to enrich a medical image.

27. The computer-implemented method of claim 26 wherein the audio-based content is descriptive content that describes a portion of the medical image.

* * * * *